United States Patent [19]
Kelsey et al.

[11] Patent Number: 5,355,418
[45] Date of Patent: Oct. 11, 1994

[54] FREQUENCY SELECTIVE SOUND BLOCKING SYSTEM FOR HEARING PROTECTION

[75] Inventors: Randy J. Kelsey, Hampstead, Md.; Larry D. Aschliman, Jacobus, Pa.

[73] Assignee: Westinghouse Electric Corporation, Pittsburgh, Pa.

[21] Appl. No.: 198,689

[22] Filed: Feb. 22, 1994

Related U.S. Application Data

[63] Continuation of Ser. No. 957,125, Oct. 7, 1992.

[51] Int. Cl.$^5$ .............................................. A61F 11/06
[52] U.S. Cl. ........................................ 381/72; 381/94; 381/68.2; 381/68.4
[58] Field of Search ....................... 381/68.2, 68.4, 72, 381/94

[56] References Cited

U.S. PATENT DOCUMENTS

| | | | |
|---|---|---|---|
| 4,187,410 | 2/1980 | Eroshkin et al. | |
| 4,187,413 | 2/1980 | Moser | |
| 4,658,426 | 4/1987 | Chabries et al. | 381/94 |
| 4,868,880 | 9/1989 | Bennett, Jr. | 381/68.2 |
| 5,027,410 | 6/1991 | Williamson et al. | |
| 5,027,412 | 6/1991 | Hayashi et al. | |
| 5,029,217 | 7/1991 | Chabries et al. | 381/68.2 |

FOREIGN PATENT DOCUMENTS

| | | | |
|---|---|---|---|
| 3132221 | 6/1991 | Japan | 381/94 |

OTHER PUBLICATIONS

Numerical Recipes: The Art of Scientific Computing (FORTRAN Version), Press, Flannery, Teukolsky & Vetterling 386–429 (1989).

*Primary Examiner*—Curtis Kuntz
*Assistant Examiner*—Mark D. Kelly

[57] ABSTRACT

A frequency selective hearing protection device and method utilizes adaptive filtering to hinder transmission of frequency components in ambient sound above a preselected threshold level. Sound frequency components which are not above the threshold level, such as normal speech, are allowed to pass. Electrical analog signals produced by a transducer are converted to a stream of digital input signals. The digital input signals are applied to a digital filter such as an FIR filter implementing a time domain difference equation. As a result, digital output signals are produced which are reconverted to analog output signals and applied to an actuator to produce audible sound. To adjust the frequency response of the invention to suppress gain at frequency components above the threshold, windows of input and output data signals are first assembled. Respective frequency domain transforms such as fast Fourier transforms provide spectrums representative of frequency component amplitudes. Any violator components exceeding the threshold level are distinguished and coefficient values of the difference equation are altered to suppress gain at those frequencies. Preferably, the coefficient values are readjusted to again allow the frequencies to pass if the threshold is not exceeded in preselected number of subsequent digital input signals.

18 Claims, 4 Drawing Sheets

FREQUENCY SELECTIVE SOUND BLOCKING SYSTEM FOR HEARING PROTECTION

This application is a continuation of application Ser. No. 07/957,125, filed Oct. 7, 1992.

BACKGROUND OF THE INVENTION

1. Field of the Invention

The present invention relates to systems for preventing discomfort and hearing loss due to high amplitude sound. More particularly, the invention relates to such a system utilizing an adaptive digital filter to selectively hinder transmission of sound frequency components above a preselected threshold level while allowing transmission of other sound frequency components.

2. Description of the Prior Art

Exposure to environments of high amplitude sound has often been a source of discomfort and hearing loss. To alleviate such problems, workers at construction sites and in industrial facilities have frequently been provided with sound blocking earplugs. While these earplugs are generally effective at reducing high power noise, the sound blockage function is nonselective. Thus, all sound is suppressed, not merely high power noise. As a result, verbal communication is also restricted.

SUMMARY OF THE INVENTION

The present invention provides a frequency selective hearing protection device and method which utilizes an adaptive filtering difference equation having a plurality of alterable coefficient values. The system selectively hinders transmission of frequency components in ambient sound having power levels above a preselected threshold. Sound frequency components which are not above the threshold level, such as normal speech, are allowed to pass.

In a sound blocking system practicing the invention, ambient sound is typically monitored by a transducer which produces an electric analog input signal. The analog input signal is then sampled by a sampler circuit to produce a stream of sampled input signals. Next, the sampled input signals are converted to digital input signals by an analog-to-digital converter. The difference equation is implemented by a digital filter which receives the digital input signals and produces filtered digital output signals. The digital output signals are then fed to a digital-to-analog converter which produces an analog output signal. Typically, the analog output signal is next filtered using a reconstruction filter and is fed to a sound actuator. As a result, the actuator produces a sound output which may be perceived.

Memory means having respective input data memory locations and output data memory locations receive and sequentially store respective windows of digital input signals and digital output signals. When the windows are assembled, frequency domain transformations are performed by transform means to produce respective spectrums representative of frequency component amplitudes. In presently preferred embodiments, fast Fourier transform principles are utilized for this purpose. Frequency components of the spectrums are then analyzed by comparator means to determine whether any violate the threshold criteria. If so, these violator components are distinguished and stored as tagged components.

Based on violator components in at least one of the spectrums, adaptive means adjust the difference equation coefficient values to suppress output gain at those frequencies. Preferably, this is accomplished by first utilizing means responsive to the respective transform means for selectively calculating a present ideal frequency response. The present ideal frequency response is then applied to inverse transform means which produces a corresponding time domain response. Windowing means implementing a window function may also be provided to smooth the time domain response. The coefficients, which correspond to time domain samples of the desired filter response, are then produced. Preferably, violation counter means are also provided to facilitate removal of gain suppression at tagged components which do not again exceed the threshold level within a preselected number of subsequent digital input signals.

DETAILED DESCRIPTION OF PRESENTLY PREFERRED EMBODIMENTS

In addition to normal filtering, operation of the invention includes monitoring for noise frequency components above a preselected threshold level and adjusting the filter characteristics to suppress those frequencies. Preferably, a record is kept of the components previously tagged as violators, and if the same frequency components do not occur above the threshold level again in a specified period of time, the filter is readjusted to allow those frequency components to pass. This feature prevents non-repetitious noise from altering the operation of the filter for an extended period of time. The user is protected from loud blasts of any type of noise by limiting the maximum amplitude at the output of the system.

Figure 1:
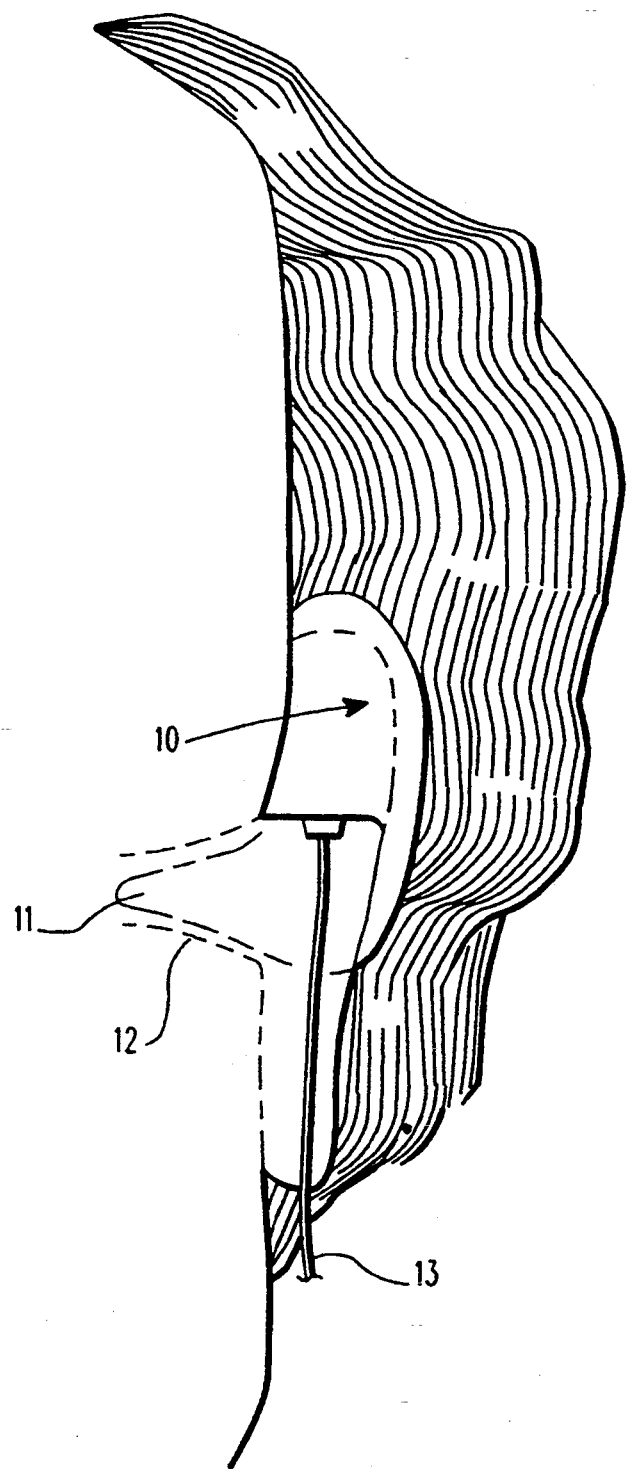
FIG. 1 illustrates an ear unit such as may be used with the invention having a portion inserted into the ear canal of a wearer to effectuate sound blocking.

For best results, the sound output heard by the user should be determined to as large an extent as practicable solely by the output of the system. Thus, referring to FIG. 1, the system may utilize an appropriate ear unit 10 having a plug portion 11 partially inserted into the ear canal 12 of the wearer. Depending on the particular implementation, all necessary components may be contained within unit 10 or may be distributed between unit 10 and an external module (not shown) via interconnecting cable 13. When worn in the manner shown, unit 10 thus performs a natural sound blocking function.

Figure 2:
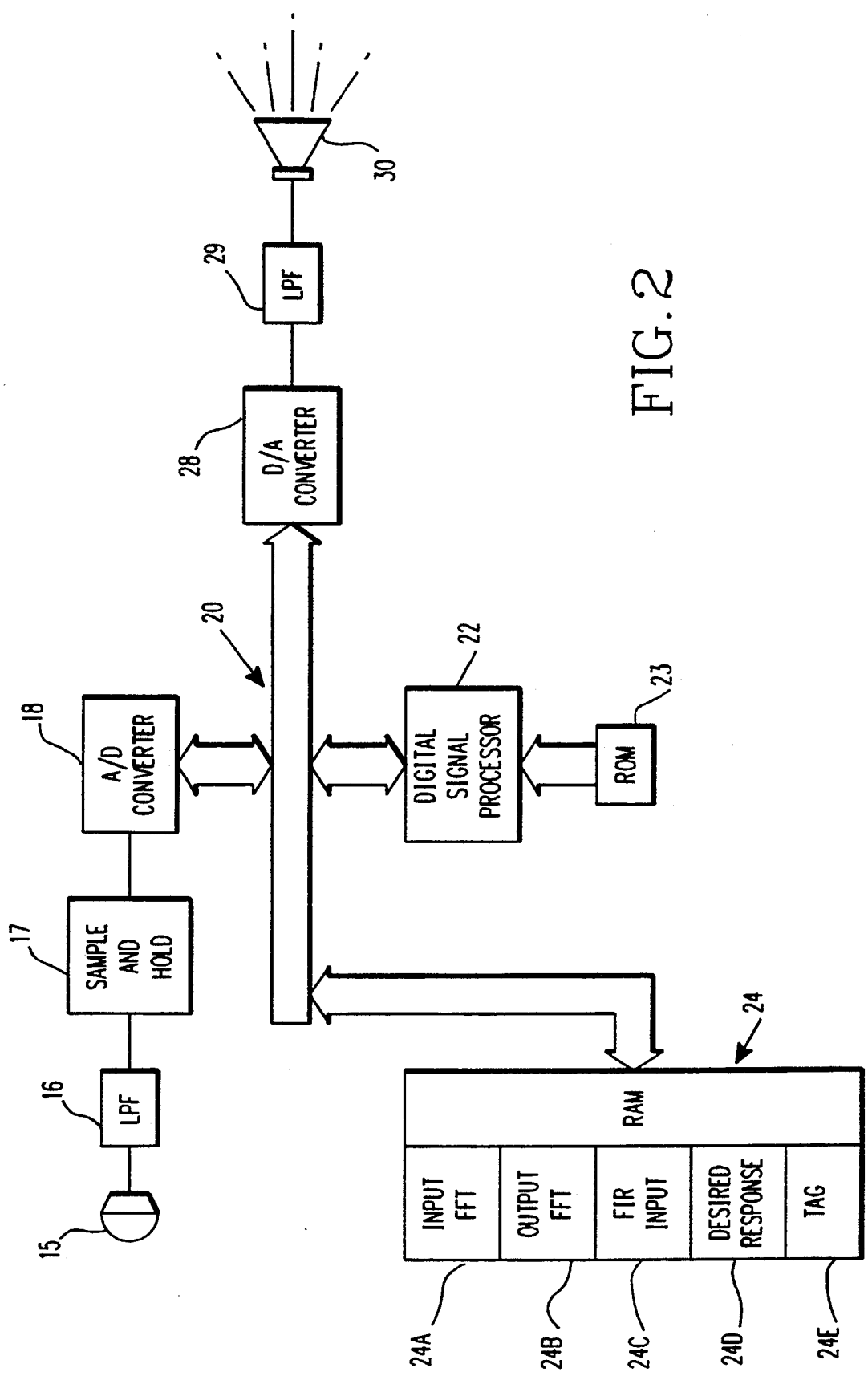
FIG. 2 is a diagrammatic representation of presently preferred hardware components for use with the hearing protection device of the invention.

FIG. 2 illustrates the interconnection of various components of the device of the invention. A microphone 15, preferably located within unit 10, monitors ambient sound and produces an analog input signal. In order to be processed according to the invention, this analog input signal must be converted to a stream of digital input signals. To prevent aliasing, the analog input signal is first band limited by low pass filter ("LPF") 16. The output of LPF 16 is then fed to sample and hold circuit 17. In accordance with the sampling theorem, the periodic sampling rate of circuit 17 is preferably at least twice the cutoff frequency of LPF 16. The stream of amplitude sampled input signals produced by circuit 17 is next fed to analog-to-digital ("A/D") converter 18. Converter 18 produces the digital input signals, which are received on bus 20.

A digital signal processor ("DSP") 22 provides timing and control of data flow along bus 20 as well as implementing the filtering operations of the invention. Read only memory ("ROM") 23 contains data representative of the quiescent system frequency response as well as the operating instructions for DSP 22. Also in electrical communication with bus 20 is a random access memory ("RAM") 24 which is divided logically into a number of banks. These are input FFT bank 24A, output FFT bank 24B, FIR input bank 24C, desired response bank 24D, and tag bank 24E. The function of the respective banks will be explained fully below. Digital output signals received from bus 20 are first passed to digital-to-analog ("D/A") converter 28. An analog output signal is fully reconstructed by passing the output of converter 28 through LPF 29 which also includes appropriate amplification. The output of LPF 29 is used to actuate speaker 30.

Figure 3:
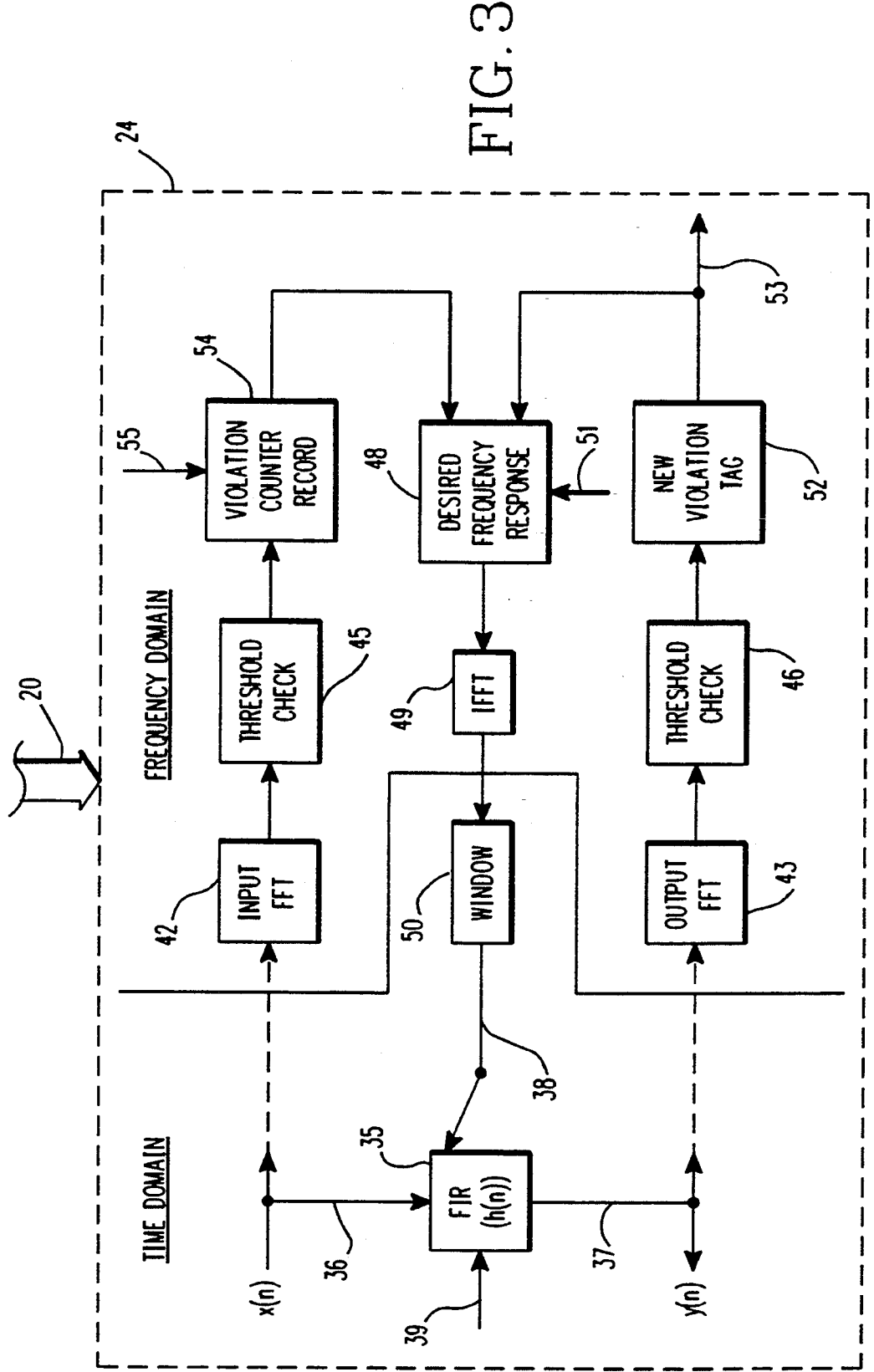
FIG. 3 is a block flow diagram illustrating presently preferred adaptive filtering operations performed by the digital signal processor of FIG. 2.

Referring to FIG. 3, the operations performed by DSP 22 are functionally illustrated. Digital filter 35 receives digital input signals on line 36 and produces corresponding digital output signals on line 37. Preferably, filter 35 is a finite impulse response ("FIR") filter. An FIR filter implements the following difference equation: $y(n) = b(1)*x(n) + b(2)*x(n-1) ... + b(N)*x(n-N-1)$, where $x(n)$ is the current sampled input signal, $x(n-1)$ is the previous sample, N is the total number of samples used by the filter, $y(n)$ is the output of the filter, and $b(1)$ etc. are the filter coefficients. From the above equation, it can be seen that the filter utilizes past inputs as well as the current input in determining the value of the output signal. The plurality of filter coefficients, which are received on line 38, thus represent the respective weights given to each of the input samples used to determine the current output signal. These past inputs, having been stored in FIR input RAM 24C, are received on line 39.

The number of samples and coefficients determine the order of the filter. Generally, a higher filter order gives better frequency response. Additional delay, however, is introduced into the system as filter order increases. This delay is given by the relationship $[((N-1)/2)(T)]$, where T is the time interval between consecutive samples. In this application, delay will be generally imperceivable to the user and may not be a significant limiting consideration. Thus, a filter order generally in the range of 128 to 512 is considered acceptable.

In order to adjust the filter coefficients to suppress gain at frequency components exceeding the threshold level, DSP 24 performs a number of functions in the frequency domain. Each digital input signal and digital output signal is respectively received and sequentially stored in input FFT bank 24A and output FFT bank 24B. Once respective windows of a predetermined number of signals have been assembled, transform means are provided at 42 and 43 to produce respective spectrums representative of frequency component amplitudes. Due to the filter delay, the samples in the input FFT bank 24A will be $(N-1)/2$ samples ahead of digital input signals taken at the same sample in the output FFT bank 24B. To compensate, the addresses are initialized to synchronize the beginning of the windows. Thus, the input FFT window will be filled before the output FFT window. The FFT window collection operates in a continuous cyclic manner. When a window is full and calculations are being performed on the data, current samples of data are placed into the next window.

Figure 4A:
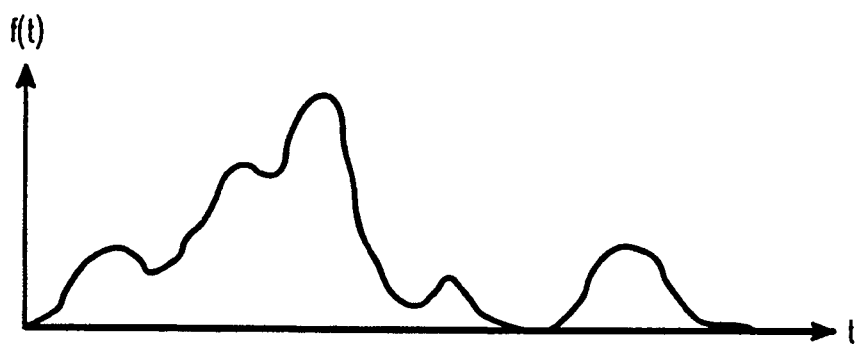
FIG. 4A is a hypothetical aperiodic electrical signal analogous to an ambient sound input.
Figure 4B:
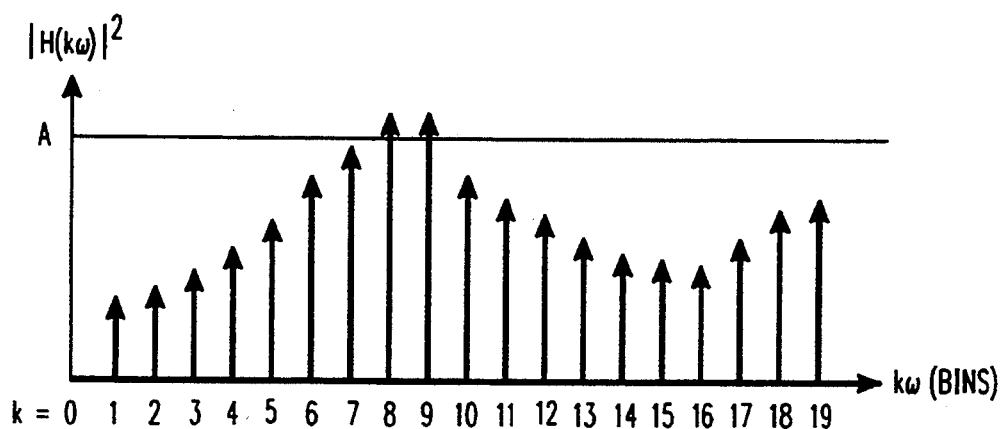
FIG. 4B is a hypothetical frequency power spectrum such as may result from spectral analysis of the waveform of FIG. 4A.

As the name of input FFT bank 24A and output FFT bank 24B suggests, transform is accomplished in presently preferred embodiments utilizing fast Fourier transform ("FFT") techniques. An FFT takes amplitude samples in the time domain and yields the power content in the frequency domain. For example, FIG. 4A illustrates a hypothetical aperiodic electrical analog signal produced at microphone 15. As described above, this signal is sampled at a periodic rate and converted to a stream of digital input signals. After a window of digital input signals has been assembled, FFT performed. As shown in FIG. 4B, FFT specifically gives power content in each of a number of frequency bins. The range of each frequency bin is dependant on the sampling rate of circuit 17 and the number of samples used in the calculation (size of the FFT window).

Comparator means 45 and 46 respectively determine whether any bin in the input FFT and output FFT exceed the threshold level. When the FFT calculations yield violator components, desired (ideal) frequency response means 48 adjust the frequency response of the filter so that gain at the offending frequencies is suppressed. This is illustrated for the example above in FIG. 4C, where the gain values of bins 8 and 9 are significantly attenuated. The time domain coefficient values are obtained from the desired frequency response by performing an inverse FFT at inverse transform means 49 and multiplying the results at windowing means 50 by a windowing function to smooth the response. A Harming windowing function is believed suitable for this purpose. The output of windowing means 50 are the adjustable filter coefficients of filter 35.

Figure 4C:
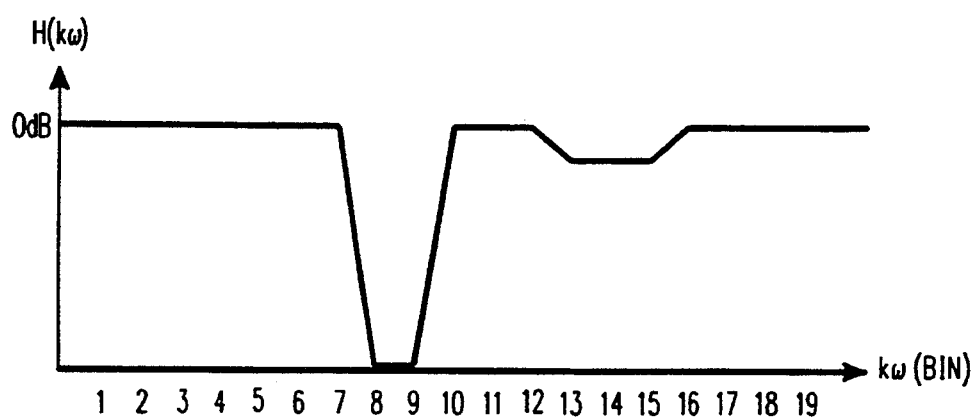
FIG. 4C is an example of an ideal frequency response characteristic which suppresses violator components in the frequency spectrum of FIG. 4B.

Typically, desired frequency response means 48 will also be preset on line 51 by ROM 23 in order to compensate for nonlinear fries which may be introduced into the overall system by system components such as microphone 15 and speaker 30. This is illustrated in FIG. 4C where the gain at bins 13 through 15 is shown slightly suppressed to compensate for a slight hypothetical system peak at these frequencies.

Frequency components exceeding the threshold criteria are distinguished (tagged) at new violation tag 52 and output on line 53 to tag bank 24E. To avoid term effects of nonrepeating loud noises, violation counter means 54 track the number of consecutive digital input signals in which the tagged components (received from tag bank 24E on line 55) do not exceed the threshold. After these components have not violated the criteria for a specified period of time (clocked by input signals), violation counter record 54 communicates with desired frequency response means 48 to readjust the filter coefficients. These components can now again pass through the system.

A hearing protection system has been provided to adaptively hinder transmission of frequencies above a threshold level, while allowing frequencies below the threshold are allowed to pass. Although certain preferred embodiments have been described and shown, it is to be understood that various other embodiments and modifications can be made within the scope of the following claims.

We claim:

1. A hearing protection device usable in environments of high amplitude sound to adaptively hinder transmission of frequencies above a threshold amplitude level while allowing transmission of frequencies below said threshold amplitude level, said device comprising:
   a transducer for receiving a sound input and producing an electrical analog input signal;
   sampler means operable to sample said electrical analog input signal at a periodic sampling rate and produce a stream of sampled input signals;
   an analog-to-digital converter receiving said sampled amplitude input signals and producing respective corresponding digital input signals;
   digital filter means implementing a time domain difference equation having a plurality of alterable filter coefficients for receiving said digital input signals and producing respective corresponding filtered digital output signals;
   memory means having respective input data memory locations and output data memory locations for receiving and sequentially storing respective windows of said digital input signal and said digital output signals;
   first transform means for receiving said window of said digital input signals and producing therefrom a first spectrum representative of input signal frequency component amplitudes;
   means for comparing frequency components of said first frequency spectrum with said amplitude threshold level and distinguishing first violator frequency components which exceed said amplitude threshold level;
   second transform means for receiving said window of said digital output signals and producing therefrom a second frequency spectrum representative of output signal frequency component amplitudes;
   means for comparing frequency components of said second frequency spectrum with said amplitude threshold level and distinguishing second violator frequency components which exceed said amplitude threshold level;
   adaptive means for adjusting said plurality of alterable filter coefficients to suppress output gain at first and second violator frequency components;
   digital-to-analog conversion means for receiving said digital output signals and producing an analog output signal; and
   an actuator for receiving said analog output signal and producing a sound output.

2. The ear protection device of claim 1 wherein said memory means further comprises violator components memory locations for storing data identifying said violator components.

3. The ear protection device of claim 2 further comprising violation counter means to facilitate removal of gain suppression at each of said violator components identified in said violator components memory locations which do not exceed the amplitude threshold level within a preselected number of subsequent digital input signals.

4. The ear protection device of claim 1 wherein said first and second transform means respectively produce said first and second frequency spectrums by implementing a fast Fourier transform.

5. The ear protection device of claim 1 wherein said digital filter is a finite impulse response filter.

6. The ear protection device of claim 5 wherein said plurality of alterable filter coefficients is generally within the range of 128 to 512 alterable filter coefficients.

7. The ear protection device of claim 1 further comprising a read only memory having stored therein initial frequency response data.

8. The ear protection device of claim 1 wherein said adaptive means includes:
   means responsive to said first and second transform means for selectively calculating a present ideal frequency response; and
   inverse transform means for receiving an output of said means responsive to said first and second transform means and selectively producing a corresponding time domain response.

9. The ear protection device of claim 8 further comprising windowing means for filtering-an output of said inverse transform means.

10. The ear protection device of claim 9 wherein said windowing means implements a Hanning windowing function.

11. A method of protecting hearing in environments of high amplitude sound by adaptively hindering transmission of frequencies having amplitudes above a threshold level while allowing transmission of frequencies having amplitudes below said threshold level, said method comprising the steps of:
   (a) monitoring ambient sound and producing a stream of representative digital input signals;
   (b) filtering said digital input signals according to a time domain difference equation having a plurality of coefficient values to produce respective digital output signals;
   (c) assembling respective first and second windows of a preselected number of said digital input signals and said digital output signals;
   (d) performing respective frequency domain transformations on data in said first and second windows to produce respective first and second spectrums representative of frequency component amplitudes;
   (e) distinguishing violator components of said first and second spectrums that exceed said threshold level;
   (f) adjusting said coefficient values in response to said violator components to thereafter suppress filter gain at the respective frequency; and
   (g) converting said digital output signals to audible sound.

12. The method of claim 11 further comprising the following steps:
   (h) readjusting said coefficient values when a frequency component amplitude in said first spectrum which has been distinguished as a violator component has not exceeded said threshold level for a selected period.

13. The method of claim 11 wherein step (f) comprises the steps of:
   (i) calculating responsive to violator components in at least one of said spectrums a protective frequency response having said violator components attenuated;

(j) performing an inverse transformation on said protective frequency response to produce a corresponding time domain response; and
(k) filtering said time domain response utilizing a windowing function.

14. The method of claim 11 wherein said time domain difference equation is a finite impulse response equation.

15. The method of claim 14 wherein said time domain difference equation has at least 128 coefficient values.

16. The method of claim 11 wherein said frequency domain transformations are fast Fourier transforms.

17. The method of claim 16 wherein said first and second spectrums each comprise at least 128 frequency bins.

18. The method of claim 16 further comprising the step between steps (c) and (d) of:
(1) synchronizing said first and second windows to account for time delay between said digital output signals and corresponding of said digital input signals introduced by said time domain difference equation.

* * * * *